United States Patent [19]
Werner

[11] Patent Number: 5,922,713
[45] Date of Patent: Jul. 13, 1999

[54] INHIBITION OF NITRIC OXIDE SYNTHASE

[76] Inventor: Ernst Werner, Hechenbergstrasse 10, A-6020 Innsbruck, Austria

[21] Appl. No.: 08/882,456

[22] Filed: Jun. 26, 1997

[51] Int. Cl.$^6$ ...................... A61K 31/495; A61K 31/505; C07D 475/08
[52] U.S. Cl. ........................... 514/249; 514/258; 544/260
[58] Field of Search ................................... 514/258, 249; 544/260

[56] References Cited

U.S. PATENT DOCUMENTS 2,667,485  1/1954  Petering .................................. 544/260

FOREIGN PATENT DOCUMENTS 4418096  11/1995  Germany .
4418097  11/1995  Germany .

OTHER PUBLICATIONS

The Journal of Biological Chemistry, vol. 269, No. 19, May 1994, pp. 13861–13866, "The Pteridine Binding Site of Brain Nitric Oxide Synthase," by Peter Klatt et al.
Neuropharmacology, vol. 11, 1994, pp. 1253–1259, "Molecular Mechanisms of Inhibition of Porcine Brain Nitric Oxide Synthase by the Antinociceptive Drug 7–Nitro–Indazole," by B. Mayer et al.
Helvetica Chimica Acta, vol. 68, 1985, pp. 1639–1643, "Pterinechemistry, A New, Regiospecific Synthesis of L–Biopterin," by Bernhard Schircks et al.
Helvetica Chimica Acta, vol. 60, Fasc. 1, 1977, pp. 211–214, "Uber Pterinchemie, A New, Regiospecific Synthesis of L–Biopterin," by Bernhard Schircks et al.
Chemistry Letters, 1984, pp. 735–738, "Highly Selective Procedure for (6R)–Tetrahydrobiopterin Cofactor." by Sadao Matsuura et al.
Journal of Allergy Clinical Immunology, vol. 99, No. 5, May 1997, pp. 624–629, "Increased Levels of Nitric Oxide Derivatives in Induced Sputum in Patients with Asthma," by Hiroshi Kanazawa et al.
Journal of Biochemistry, vol. 315, 1996, pp. 57–63, "Overexpression of Neuronal Nitric Oxide Synthase in Insect Cells Reveals Requirement of Haem for Tetrahydrobiopterin Binding," Barbara M. List et al.
Archives of Biochemistry and Biophysics, vol. 128, 1968, pp. 1–5, "Nuclear Magnetic Resonance Studies of Some Biologically Active Dihydropterins," Takeshi Fukushima et al.
Journal of Biological Chemistry, vol. 228, 1957, pp. 1031–1038, "Enzymatic Reduction of Folic Acid and Dihydrofolic Acid to Tetrahydrofolic Acid," by Sidney Futterman.
Werner, Ernst R. et al., "Identification of the 4–amino analogue of tetrahydrobiopterin as a dihydropteridine reductase inhibitor and a potent pteridine antagonist of rat neuronal nitric oxide synthase," Biochem. J., vol. 320, Nov. 1996, 193–196.
Chemical Abstracts 66: 75978 W (1967).
Rembold, H. et al., "Synthesis of Biopterin, Neopterin, and Analogs," IN : Methods in Enzymology, Vitamins and Coenzymes, vol. XVIII, Part B, Academic Press, NY, 1971 pp. 670–678.

Primary Examiner—John Pak
Attorney, Agent, or Firm—Lorusso & Loud

[57] ABSTRACT

The invention comprises a method of effecting nitric oxide synthase inhibition, and nitric oxide level reduction by use of a composition of the structure

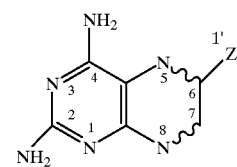

wherein Z is an hydroxyl carbon at 1' of the formula CH(OH)—X;
wherein X is selected from the group consisting of CH(OH)—CH3, (CH(OH))$_n$—Y, and (CH(OH))$_n$—CH2$_n$—W;
wherein Y is hydrogen, or lower alkyl, W is hydrogen or hydroxyl, and n is 1–20;
and the 5–6 and 7–8 bonds are each either a single bond or a double bond,
and pharmaceutically acceptable salts thereof (collectively, "C1' aminobiopterin"), and compositions useful in such method.

13 Claims, No Drawings

INHIBITION OF NITRIC OXIDE SYNTHASE

FIELD OF THE INVENTION

The invention comprises a method of effecting nitric oxide synthase inhibition, and nitric oxide level reduction by use of a composition of the structure

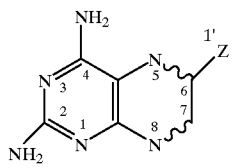

wherein Z is an hydroxyl carbon at 1' of the formula CH(OH)—X;

wherein X is selected from the group consisting of CH(OH)—CH3, (CH(OH))$_n$—Y, and (CH(OH))$_n$—CH2$_n$—W;

wherein Y is hydrogen, or lower alkyl, W is hydrogen or hydroxyl, and n is 1–20;

and the 5–6 and 7–8 bonds are, each, either single bonds or double bonds, and pharmaceutically acceptable salts thereof (collectively, "C1' aminobiopterin"). Note that not all hydrogen molecules are shown.

BACKGROUND OF THE INVENTION

In recent years therapeutic medicine has become increasingly concerned with the physiological role of nitric oxide, NO. "Overproduction" of NO has been implicated in pathological conditions such as sepsis and cellular toxicity observed in dopanergic neurons with Parkinson's disease. In vivo, nitric oxide is formed by nitric oxide synthase. A number of nitric oxide synthase modulators have been identified, with particular reference to nitric oxide synthase inhibitors.

This invention is particularly concerned with nitric oxide synthase activity modification with particular reference to 2,4-diamino-5,6,7,8-tetrahydro-6-(L-erythro-1,2-dihydroxylpropyl)pteridine (both as to the 6R form and the 6S form), also termed tetrahydroaminobiopterin, a nitric oxide synthase inhibitor as represented in Table I (I). Attention is drawn to 2,4-diamino-5,6,7,8-tetrahydro-6-hydroxymethyl pteridine, a nitric oxide synthase inhibitor as represented in Table I (III). See, DE 44 18 097.

In one embodiment, this invention is concerned the nitric oxide synthase inhibitor, 2,4-diamino-7,8-dihydro-6-(L-erythro-1,2-dihydroxylpropyl)pteridine, also termed 7,8 dihydroaminobiopterin, or H$_2$aminobiopterin, as represented in Table I (IV).

Other nitric oxide synthase inhibitors are L-NMMA, L-NAME, NG, NG-dimethyl-L-arginine, L-NMEA (NG-monoethyl-L-arginine), L-NIO (N-imino-ornithine, L-iminoethyl-lysine, L-thiocitrulline, aminoguanadine, iminobiotin L-amino arginine, 7-nitroindazol, NG-methylarginine, and NG-nitroarginine. Attention is also drawn to pteridines as disclosed in DE 44 18 096, and the tetrahydropteradines of DE 44 18 097.

Without being bound by any particular theory or mechanism of action, it is noted that nitric oxide synthase tightly binds the 5,6,7,8,-tetrahydro-L-erythro-biopterin moiety ("tetrahydrobiopterin"). And further that, in vivo, availability of tetrahydrobiopterin appears to be a rate limiting step. Thus, the addition of exogenous tetrahydrobiopterin is required for nitric oxide synthase to reach full activity. This invention is drawn to substances and methods which exploit this finding.

SUMMARY OF THE INVENTION

This invention comprises a method of inhibiting nitric oxide synthesis in a nitric oxide synthase utilizing organism by contacting nitric oxide synthase with a therapeutically effective amount of composition of the formula

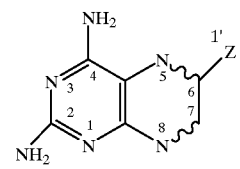

wherein Z is an hydroxyl carbon at 1' of the formula CH(OH)—X;

wherein X is selected from the group consisting of CH(OH)—CH3, (CH(OH))$_n$—Y, and (CH(OH))$_n$—CH2$_n$—W;

wherein Y is hydrogen, or lower alkyl, W is hydrogen or hydroxyl, and n is 1–20;

and the 5–6 and 7–8 bonds are, each, either single bonds or double bonds, and pharmaceutically acceptable salts thereof (collectively, "C1' aminobiopterin"). Note that not all hydrogen molecules are shown.

TABLE I

| Structure | Name |
|---|---|
| | tetrahydroaminobiopterin (I) |
| 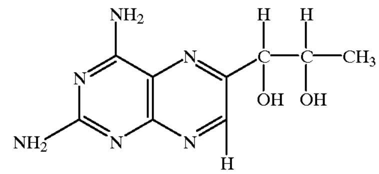 | aminobiopterin (II) |
| 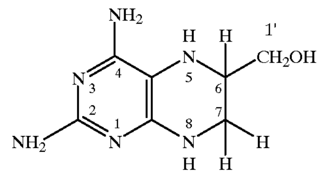 | 2,4,-diamino-5,6,7,8-tetra hydro-6-hydroxymethyl pteridine (III) |
| 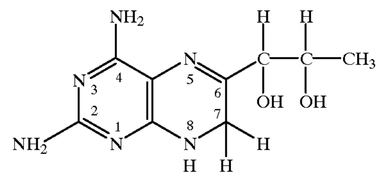 | 2,4,-diamino-7,8-dihydro-6-(L-erythro-1,2,dihydroxy propyl)pteridine (IV) |

Particular reference is made to the C1' aminobiopterins tetrahydroaminobiopterin (I) in either the 6R or 6S form and 2,4,-diamino-7,8-dihydro-6-(L-erythro-1,2-dihydroxypropyl)pteridine. The N5 and N8 are charge sites for salt forms.

In one embodiment the method includes administering a therapeutically effective amount in concentrations of about 100 to about 500 $\mu$M, as well as the therapeutically effective amount administered from about 4 to about 400 mg/kg body weight. In addition, the method comprises the therapeutically effective amount administered in about a 10 to about 150 mg/kg bolus injection, and the therapeutically effective amount administered at about 3 to about 15 mg/kg/hr.

This invention further comprises a composition of the formula

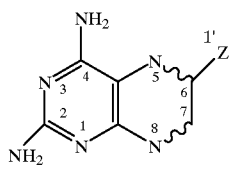

wherein Z is an hydroxyl carbon at 1' of the formula CH(OH)—X;

wherein X is selected from the group consisting of CH(OH)—CH3, (CH(OH))$_n$—Y, and (CH(OH))$_n$—CH2$_n$—W;

wherein Y is hydrogen, or lower alkyl, W is hydrogen or hydroxyl, and n is 1–20;

and the 5–6 and 7–8 bonds are each either a single bond or a double bond, and pharmaceutically acceptable salts thereof.

In a specific embodiment, the composition is tetrahydroaminobiopterin (I) including the 6R and 6S configurations. In yet another embodiment the composition is 2,4,-diamino-7,8-dihydro-6-(L-erythro-1,2-dihydroxypropyl) pteridine. Particular note is made of the compositions in unit dosage form and accompanied by a suitable pharmaceutical carrier.

DETAILED DESCRIPTION OF THE INVENTION

This invention is particularly understood with resort to the following definitions:

A. "Nitric oxide" shall mean NO, mononitrogen monoxide.
B. "Nitric oxide synthase" shall mean an enzyme capable of forming NO. In mammals, at least three types of nitric oxide synthase have been identified which form NO from L-arginine. These forms are neuronal, endothelial, and inducible. Others forms are know in the art. As used herein, nitrogen oxide synthase is to be expansively understood to include all such nitric oxide forming enzymes.
C. "Nitric oxide synthase utilizing organism" is an expansive term including all mammals as well as all other organisms which use NO as a signal or regulatory transmitter or modulator of a biological process. Specific note is made of other species including birds, insects and single celled organisms.
D. "Contacting" as used in reference to C1' aminobiopterin shall mean causing C1' aminobiopterin to be physically available for binding to a nitric oxide synthase such as by placing C1' aminobiopterin in the same fluid as the nitric oxide synthase. By way of example, adding tetrahydroaminobiopterin (I) in vivo to the blood circulation of a subject would place tetrahydroaminobiopterin (I) in contact with the nitric oxide synthase of the cells of the circulatory system and cells served by the circulators system.
E. "S" and "R" are references to stereomeric or enantiomeric configurations as the terms are commonly used in the art with particular reference to IUPAC nomenclature.
F. "Lower alkyl" shall mean an alkyl of from 1 to 9 carbons.
G. "Therapeutically effective amount" as to a drug dosage, shall mean that dosage that provides detectable nitric oxide synthase inhibition in a subject wherein such level of reduction achieves an amelioration of a pathology arising from pre-administration nitric oxide synthase activity levels or pre-administration nitric oxide levels. It is emphasized that the specific conditions will respond differently to varying levels of nitric oxide or nitric oxide synthase activity. That is, asthmatic response may be markedly improved with a modest—5–10%—reduction in nitric oxide synthase activity or nitric oxide levels, whereas amelioration of chronic neurologic degeneration may require at least 20% reduction. It is to be further understood that drug dosages are, in particular instances, measured as oral dosages, or parenteral or inhaled dosages or with reference to drug levels as measured in blood. Ultimately, it is the empirical observation by one skilled in the art of the cells or subject being treated which directs treatment to a more effective dosage.

Particular note is made of therapeutic use of concentrations of about 100 to about 500 $\mu$M, and, more generally, wherein cells to be treated are exposed to concentrations of from about 25 to about 1000 $\mu$M. Particular note is made of therapeutic use of concentrations of (IV) wherein subjects to be treated are administered from about 4 to about 400 mg/kg body weight, with particular reference to about 20 to about 80 mg/kg, and further reference to about 30 to about 70 mg/kg. Administration may be in a singly daily bolus or in about two to 4, or eight or more administrations. In some embodiments, dosing is continuous such as by an implant which releases drug, or by continuous infusion pump. Attention to the clearance rate or half-life of a particular C1-aminobiopterin is one means by which one skilled in the art maintains a particular circulating drug level. Chronic maintenance dosing from daily, to every other day, to weekly is noted is noted. A subject may be maintained for months or years or more.

Tetrahydroaminobiopterin (I) or 2,4-diamino-7,8-dihydro-6-(L-erythro-1,2-dihydroxylpropyl)pteridine exhibits an affinity for nitric oxide synthases which is higher than for the naturally occurring cofactor, tetrahydrobiopterin. This affinity is about 20-fold higher for rat neuronal nitric oxide synthase and about 2.5-fold higher for inducible murine nitric oxide synthase. These determinations are assayed with binding of tritiated tetrahydroaminobiopterin according to the method of Klatt et al., "The pteridine binding site of brain nitric oxide synthase," *J.Biol.Chem.*, 269:13861–13866 (1994), the teachings of which are incorporated herein by reference.

It has been discovered that C1' tetrahydroaminobiopterin inhibits the stimulation of NOSs by 10 $\mu$M tetrahydrobiopterin with an IC$_{50}$ (50% inhibitory concentration) of 1 $\mu$M (rat neuronal NOS), or 7 $\mu$M (murine inducible NOS) as assayed by formation of tritiated citrulline from tritiated L-arginine according to Mayer, et al., "Molecular mechanisms of inhibition of porcine brain nitric oxide synthase by the antinociceptive drug 7-nitro-indazole," *Neuropharmacology,* 33:1253–1259 (1994), the teachings of which are incorporated herein by reference. In tissue culture tetrahydroaminobiopterin (I) reduced the formation of nitrites (a breakdown product of nitric oxide) when formation was triggered in murine NIH-3T3 by treatment with a combination of murine interferon-γ (250 U/ml) and lipopolysaccharide (1 μg/ml) ("LPS"). Treatment resulted in an $IC_{50}$ of 13 μM, without apparent cellular toxicity. Similar efficient inhibition of NO production was also observed when tetrahydroaminobiopterin (I) was added one day after interferon-γ/LPS stimulus. The inhibitory effect of tetrahydroaminobiopterin (I) on NOS was also demonstrated in in vitro application such as in cultivated porcine endothelial cells ($IC_{50}$ at 100 μM). Tetrahydroaminobiopterin (I) is highly specific for NOSs. In one embodiment, rat liver phenylalanine-4-hydroxylase was inhibited by 1 mM tetrahydroaminobiopterin only 30% irrespective of the tetrahydroaminobiopterin concentrations used (3–300 μM). $IC_{50}$ of tetrahydroaminobiopterin (I) for sheep liver dihydropterin reductase is 20 μM, again irrespective of the tetrahydroaminobiopterin concentrations used.

C1' tetrahydroaminobiopterin is thus found to be useful in physiological conditions, pathologies, or disease states in which treatment by reduction of NO production is indicated. Particular reference is made to Parkinson's disease, Alzheimer's disease, septic shock, and asthma, and neurodegenerative diseases.

A number of syntheses are useful in preparing the C1' tetrahydroaminobiopterins of this invention. Reference is made to Schircks et al., "Neue Regiospezifische Synthese von L-Biopterin und dessen Derviaten," Ph.D. Thesis, University of Zurich, Switzerland (1978), the teachings of which are incorporated herein by reference. Tetrahydroaminobiopterin (I) is synthesized by the steps of preparing 2,4-diamino-6-(L-erythro-1,2-dihydroxypropyl)pteridine (also Is termed aminobiopterin) of structure (II) in Table I according to the method of B. Schircks et al., Helv. Chim. Acta, 68:1639–1643 (1985), and B. Schircks et al., Helv. Chim. Acta, 60(Fasc. 1):211–214 (1977), the teachings of which are incorporated herein by reference. The aminobiopterin is then hydrogenated and split into two (6R and 6S) diastereomers according to the method of S. Matsuura et al., Chem. Lett. (Chemical Society of Japan), 735–738 (1984), the teachings of which are incorporated herein by reference. This step yields a white powder of tetrahydroaminobiopterin dihydrochloride. On a 250 mm long, 4 mm i.d. strong cation exchange HPLC column (Nucleosil 10 SA, Marchery Nagl, Düren, F. R. G.) eluted with 0.1M potassium phosphate buffer, pH 6.8, containing 5 mM dithioerythrol at a flow rate of 0.8 ml/min, retention times of 16.5 min. and 19.8 min. are observed for the 6R and 6S isomers (respectively) which are detected by absorption at 254 nm.

The therapeutic use of C1' aminobiopterin is facilitated by its low toxicity, both in vitro and in vivo. A useful in vitro toxicity screen which is predictive of in vivo response was to use cultured 3T3 murine fibroblasts. Cultured 3T3 murine fibroblasts exposed to 250 μM concentrations of tetrahydroaminobiopterin (I) showed no cytotoxicity up to 48 hours. In an in vivo test, intraperitoneal injection of a solution containing 10 mg of tetrahydroaminobiopterin (I) dihydrochloride caused no toxicity in Sprague-Dawley rats (240–250 g body weight).

Particular note is made of therapeutic use of concentrations of about 100 to about 500 μM, and, more generally, wherein cells to be treated are exposed to concentrations of from about 25 to about 1000 μM. Particular note is made of therapeutic use of concentrations of (IV) wherein subjects to be treated are administered from about 4 to about 400 mk/kg body weight, with particular reference to about 20 to about 80 mg/kg, and further reference to about 30 to about 70 mg/kg. Administration may be in a singly daily bolus or in about two to 4 or eight or more administrations. In some embodiments dosing is continuous such as by an implant which releases drug, or by continuous infusion pump. Attention to the clearance rate or half-life of a particular C1-aminobiopterin is one means by which one skilled in the art maintains a particular circulating drug level. Chronic maintenance dosing from daily, to every other day, to weekly is noted is noted. A subject may be maintained for months or years.

In some instances, the control of nitric oxide synthase, and ultimately of nitric oxide levels, will vary with the particular condition of a subject and the degree of anomalous enzymatic activity. These will further vary over time. Determination of exact dosages require the observation of a skilled practitioner in the art. In particular embodiments a beginning dosage generally equivalent to NG monomethyl arginine are conveniently administered, and then varied based upon the empirical response of the subject. Thus, an initial administration of about 10 to about 150 mg/kg bolus injection, and about 3 to about 15 mg/kg/hr for continuous are useful initial dosage regimens.

In addition, in some instances, the measurement of nitric oxide levels before and during therapy is a useful step to determine the degree of variation of nitric oxide production. By way of nonlimiting example, in asthmatics being treated, nitric oxide levels are conveniently monitored in asthmatic sputum. Kanazawa, H. et al., J. Allergy Clin. Immunol., 99:624–629 (1997) the teachings of which are incorporated herein by reference. In other embodiments, monitoring plasma or other fluids or tissues is indicative of therapeutic efficacy.

EXAMPLE 1

NO synthase activity: NO synthase activity was measured as the formation of [2,3,4,5-$^3$H]citrulline from L-[2,3,4,5-$^3$H]arginine. This was conducted by the method of Mayer, et al., "Molecular mechanisms of inhibition of porcine brain nitric oxide synthase by the antinociceptive drug 7-nitroindazole," Neuropharmacology, 33:1253–1259 (1994). Incubation mixtures (0.1 ml) contain 50 mM triethanolamine/HCl buffer, pH 7.0, 0.1 μg purified recombinant rat neuronal NO synthase (tetrahydrobiopterin-free, prepared according to the teachings of List et al., Biochem. J., 315:57–63 (1996)), the teachings of which are incorporated herein by reference., 0.1 mM L-2,3,4,5-$^3$H]arginine (approx 6000 counts per minute). 0.5 mM $CaCl_2$, 10 μg/ml calmodulin, 0.2 mM NADPH (nicotinamide dinucleotide phosphate, reduced form), 10 μM 6R-tetrahydrobiopterin, 0–1000 μM NO synthase inhibitor, 5 μM flavin adenine dinucleotide("FAD"), 5 μM flavin mononucleotide ("FMN"), and 0.2 mM 3-[3-chloramidopropyl) dimethylamonio]-1-propanesulfonate ("CHAPS"). After incubation for 10 minutes at 37° C., the reaction is stopped by the addition of 0.9 ml 20 mM sodium acetate buffer, pH 5.5, containing 1 mM L-citrulline. The mixture is then applied to ion exchange resin columns (Dowex AG50W-XB, Dow Chemical, Midland, Mich.), the eluate and 1 ml water for washing the column are collected. Next, 7 ml scintillation cocktail are added and the radioactivity is determined. The radioactivity detected by scintillation corresponds to the amount of L-citrulline formed in the NO synthase reaction.

Table II shows the results for tetrahydroaminobiopterin (I), and 7,8-dihydroaminobiopterin (IV) which, at less than 3 μM and 10 μM, respectively, show more than 50% inhibition of NO synthase activity. This compares favorably with the known compound 2,4-diamino-5,6,7,8-tetrahydro-6-hydroxymethyl pteridine (III) for which 1000 μM was required for inhibiting more than 50% of NO synthase activity in the same experimental setting.

EXAMPLE 2

Nitric oxide synthase is induced in 3T3 fibroblasts from mice ($1 \times 10^5$/ml) by a mixture of LPS (055:b5 from *E. coli.*), 1 μg/ml) and murine interferon-γ (50 U/ml). The cells were cultured with and without inhibitors for 48 hours, and nitrite was determined in culture supernatants as a measure of NO formation by the cells. The ratio of nitrite to nitrate, the second product of decomposition of NO, remains constant by treatment with the inhibitor. Nitrite determination was carried out using the Greiss Ilosvay's reagent, which was mixed with an equal volume of culture supernatant and the amount of dye formed was measured by UV absorption at 550 nm in a microplate reader. Table III presents the results, which, like Table II, disclose that tetrahydroaminobiopterin (I) is a more potent NO synthase inhibitor than 2,4-diamino-5,6,7,8-tetrahydro-6-hydroxymethyl pteridine (III). Challenge with 7.5 μM of (I) yielded 44% inhibition, whereas no activity by (III) was observed at 7.5 μM. Thus, tetrahydroaminobiopterin (I) is a therapeutically superior NO synthase inhibitor than 2,4-diamino-5,6,7,8-tetrahydro-6-hydroxymethyl pteridine (III).

TABLE II

Inhibition of recombinant rat neuronal NO synthase by the inhibitors tetrahydroaminobiopterin (I), 2,4-diamino-7,8-dihydro-6-(L-erythro-1,2-dihydroxypropyl)pteridine (IV), and 2,4-diamino tetrahydro 6-hydroxymethyl pteridine (III)

| Inhibitor | conc. (μM) | NO synthase activity (nmol/mg/min) | % inhibition |
| --- | --- | --- | --- |
| none |  | 298 | 0 |
| (I) | 0.01 | 279 | 6 |
| (I) | 0.1 | 262 | 12 |
| (I) | 1.0 | 181 | 39 |
| (I) | 3.0 | 125 | 58 |
| (I) | 10 | 72 | 76 |
| (I) | 30 | 50 | 83 |
| (I) | 100 | 35 | 88 |
| (I) | 1000 | 24 | 92 |
| (IV) | 0.01 | 294 | 0.3 |
| (IV) | 0.1 | 283 | 4 |
| (IV) | 1.0 | 242 | 18 |
| (IV) | 10 | 110 | 64 |
| (IV) | 100 | 48 | 82 |
| (IV) | 1000 | 25 | 92 |
| none |  | 334 | 0 |
| (III) | 0.01 | 325 | 3 |
| (III) | 0.1 | 318 | 5 |
| (III) | 1.0 | 306 | 8 |
| (III) | 3.0 | 304 | 9 |
| (III) | 10 | 316 | 5 |
| (III) | 30 | 319 | 4 |
| (III) | 100 | 274 | 18 |
| (III) | 1000 | 136 | 60 |

EXAMPLE 3

Synthesis of 2,4-diamino-7,8-dihydro-6-(L-erythro-1,2-dihydroxylpropyl)pteridine, also termed 7,8 dihydroaminobiopterin, or $H_2$aminobiopterin, as represented in Table I (IV) is accomplished using aminobiopterin (II) as a starting material. Aminobiopterin is reacted with dithionite according to the method of Futterman, "Enzymatic reduction of folic acid and dihydrofolic acid to tetrahydrofolic acid," *J.Biol.Chem.*, 228:1031–1038 (1957), with modification according to Fukushima & Akino, "Nuclear magnetic resonance studies of some biologically active dihydropterins," *Arch. Biochem. Biophys.*, 128:1–5 (1968), the teachings of which are incorporated herein by reference.

In one method, 250 mg of 4-aminobiopterin (II) is suspended in 50 ml water. To this suspension is added 1 g $Na_2S_2O_4$, and the mixture is incubated at 60° C. for 40 minutes. The solution is evaporated to about 15 ml and applied to a cellulose column. The column is eluted with water and the fractions containing 7,8-dihydroaminobiopterin are lyophilized to dryness. About 50 mg of 7,8-dihydroaminobiopterin with a purity of about 95% (measured by HPLC) is obtained.

HPLC is run in a 250 mm long column with a 4.6 mm inner diameter (Whatman Partisil 10 SCX, Whatman, Maidstone U.K.) which is eluted with 50 mM $Na_2HPO_4$, pH 3, at a flow rate of 1.5 ml/min. Detection is performed by UV-absorption at 254 nm. Retention times are: 5.3 minutes for 7,8-dihydro aminobiopterin, 5.0 minutes for aminobiopterin, 5.6 minutes for 6R tetrahydroaminobiopterin, and 6.4 minutes for 6S tetrahydroaminobiopterin.

TABLE III

Inhibition of nitrite formation by interferon-γ/LPS stimulated murine 3T3 fibroblasts cultured in the presence of tetrahydroaminobiopterin (I) and 2,4,-diamino tetrahydro 6-hydroxymethyl pteridine (III)

| Inhibitor | conc. (μM) | % inhibition |
| --- | --- | --- |
| none |  | 0 |
| (I) | 7.8 | 44 |
| (I) | 15.6 | 65 |
| (I) | 31.2 | 77 |
| (I) | 62.5 | 88 |
| (III) | 7.8 | 0 |
| (III) | 15.6 | 8 |
| (III) | 31.2 | 16 |
| (III) | 62.5 | 50 |

The compositions of this invention possess valuable pharmacological properties. They include inhibition of nitric oxide synthase in its several forms, and the reduction of nitric oxide levels in cells and in subjects, with particular reference to such effect in the field of neurodegenerative diseases such as Alzheimer's and Parkinson's disease, and in asthma. This effect can be demonstrated, for example, using the method of the above noted examples.

Thus, these compositions can be used to treat; Parkinsonism; Alzheimer's disease and asthma. Administration is contemplated to include chronic, acute or intermittent regimens.

The compositions are particularly useful as for maintenance therapy for chronic nitric oxide suppression.

In addition, the compositions can be used in in vitro and in vivo methodologies, including diagnostics (e.g., as a test for nitric oxide level sensitive conditions of unknown etiology). In some embodiments, tissues, cells or material treated in vitro will, thereafter, be reintroduced into a subject (which need not be the source of origin of the tissue, cells or material). Compounds of the present invention are also useful in diagnostics and screening procedures.

The compositions of this invention are generally administered to animals, including but not limited to mammals, fish, avians, etc., including humans.

The pharmacologically active compositions of this invention can be processed in accordance with conventional methods of Galenic pharmacy to produce medicinal agents for administration to patients, e.g., mammals including humans.

The compositions of this invention can be employed in admixture with conventional excipients, i.e., pharmaceutically acceptable organic or inorganic carrier substances suitable for parenteral, enteral (e.g., oral or inhalation) or topical application which do not deleteriously react with the active compositions. Inhalation in nublized form for treatment of asthma is particularly noted. Suitable pharmaceutically acceptable carriers include but are not limited to water, salt solutions, alcohols, gum arabic, vegetable oils, benzyl alcohols, polyethylene glycols, gelatine, carbohydrates such as lactose, amylose or starch, magnesium stearate, talc, silicic acid, viscous paraffin, perfume oil, fatty acid esters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compositions. They can also be combined where desired with other active agents, e.g., vitamins.

In some embodiments of the present invention, dosage forms include instructions for the use of such compositions.

For parenteral application, particularly suitable are injectable, sterile solutions, preferably oily or aqueous solutions, as well as suspensions, emulsions, or implants, including suppositories. Ampoules are convenient unit dosages.

Also for parenteral application, particularly suitable are tablets, dragees, liquids, drops, suppositories, or capsules. A syrup, elixir, or the like can be used wherein a sweetened vehicle is employed.

Sustained or directed release compositions can be formulated, e.g., liposomes or those wherein the active component is protected with differentially degradable coatings, e.g., by microencapsulation, multiple coatings, etc. It is also possible to freeze-dry the new compositions and use the lyophilizates obtained, for example, for the preparation of products for injection.

For topical application, there are employed as nonsprayable forms, viscous to semi-solid or solid forms comprising a carrier compatible with topical application and having a dynamic viscosity preferably greater than water. Suitable formulations include but are not limited to solutions, suspensions, emulsions, creams, ointments, powders, liniments, salves, etc., which are, if desired, sterilized or mixed with auxiliary agents, e.g., preservatives, stabilizers, wetting agents, buffers or salts for influencing osmotic pressure, etc. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., a Freon.

Generally, the compositions of this invention are dispensed in unit dosage form comprising about 10 to about 150 mg/kg in a pharmaceutically acceptable carrier per unit dosage. They are incorporated in topical formulations in concentrations of about 5 to 20 weight percent.

The dosage of the compositions according to this invention generally are from about 3 mg/kg/hr by infusion to about 10 mg/kg/hr, and preferably from about 6 mg/kg/hr to about 8 mg/kg/hr, when administered to patients, e.g., humans to treat (e.g., subjects with progressive or chronic neurological disorders).

It will be appreciated that the actual preferred amounts of active compositions in a specific case will vary according to the specific compositions being utilized, the particular compositions formulated, the mode of application, and the particular situs and organism being treated. Dosages for a given host can be determined using conventional considerations, e.g., by customary comparison of the differential activities of the subject compositions and of a known agent, e.g., by means of an appropriate, conventional pharmacological protocol.

I claim:

1. A method of inhibiting nitric oxide synthesis in a nitric oxide synthase utilizing organism by contacting nitric oxide synthase with a therapeutically effective amount of a compound of the formula

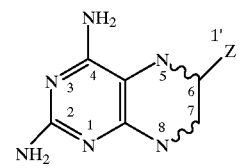

wherein Z is a hydroxyl carbon at 1' of the formula CH(OH)—X;

wherein X is selected from the group consisting of CH(OH)—CH3, (CH(OH))$_n$—Y, and (CH(OH))$_n$—(CH$_2$)$_n$—W;

wherein Y is hydrogen, or lower alkyl, W is hydrogen or hydroxyl, and n is 1–20;

and the 5–6 and 7–8 bonds are, each, either a single bond or a double bond, and pharmaceutically acceptable salts thereof.

2. The method of claim 1 wherein the compound is tetrahydroaminobiopterin (I).

3. The method of claim 2 wherein tetrahydroaminobiopterin is in the 6S form.

4. The method of claim 2 wherein tetrahydroaminobiopterin is in the 6R form.

5. The method of claim 1 wherein the compound is 2,4,-diamino-7,8-dihydro-6-(L-erythro-1,2-dihydroxypropyl)pteridine.

6. The method of claim 1 wherein the therapeutically effective amount is administered in concentrations of about 100 to about 500 μM.

7. The method of claim 1 wherein the therapeutically effective amount is administered from about 4 to about 400 mg/kg body weight.

8. The method of claim 1 wherein the therapeutically effective amount is administered in about a 10 to about 150 mg/kg bolus injection.

9. The method of claim 1 wherein the therapeutically effective amount is administered at about 3 to about 15 mg/kg/hr.

10. A compound of the formula

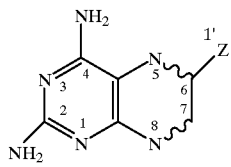

wherein Z is a hydroxyl carbon at 1' of the formula CH(OH)—X;
wherein X is selected from the group consisting of CH(OH)—CH3, (CH(OH))$_n$—Y, and (CH(OH))$_n$—(CH$_2$)$_n$—W;
wherein Y is hydrogen, or lower alkyl, W is hydrogen or hydroxyl, and n is 1–20;
and the 5–6 and 7–8 bonds are each either a single bond or a double bond,
and pharmaceutically acceptable salts thereof provided that when both 5–6 and 7–8 bonds are double bonds, Z is not (CH(OH))$_2$—CH$_3$, (CH(OH))$_2$—CH$_2$(OH), or ((CH(OH))$_{2-3}$—CH$_2$(OH).

11. The compound of claim 10 being tetrahydroaminobiopterin (I).

12. The compound of claim 11 in the 6R configuration.

13. The compound of claim 10 being 2,4,-diamino-7,8-dihydro-6-(L-erythro-1,2-dihydroxypropyl)pteridine.

* * * * *